United States Patent
Patel et al.

(10) Patent No.: US 6,215,015 B1
(45) Date of Patent: Apr. 10, 2001

(54) CATALYST COMPOSITION AND METHOD FOR PRODUCING DIARYL CARBONATES, USING BISPHOSPHINES

(75) Inventors: Ben Purushotam Patel, Albany; Grigorii Lev Soloveichik, Latham; John Yaw Ofori, Niskayuna, all of NY (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/550,202

(22) Filed: Apr. 17, 2000

(51) Int. Cl.[7] .................................................... C07C 68/00
(52) U.S. Cl. ........................ 558/274; 558/271; 558/272; 558/273; 502/162
(58) Field of Search ............................................... 558/274

(56) References Cited

FOREIGN PATENT DOCUMENTS

| 736512A1 | 10/1996 | (EP) . |
| 8466795 | 6/1989 | (JP) . |
| 84666796 | 5/1996 | (JP) . |

*Primary Examiner*—Michael G Ambrose
(74) *Attorney, Agent, or Firm*—Noreen C. Johnson; Douglas E. Stoner

(57) ABSTRACT

Hydroxyaromatic compounds such as phenol are carbonylated with oxygen and carbon monoxide in the presence of a catalyst system comprising a Group VIIIB metal, preferably palladium; an iodide salt, preferably sodium iodide; and at least one organic bisphosphine such as 1,3-bis(diphenylphosphino)propane or 1,4-bis(diphenylphosphino)butane. The catalyst system also preferably contains a compound of cerium or lead.

19 Claims, 1 Drawing Sheet

CATALYST COMPOSITION AND METHOD FOR PRODUCING DIARYL CARBONATES, USING BISPHOSPHINES

BACKGROUND OF THE INVENTION

This invention relates to the preparation of diaryl carbonates by carbonylation. More particularly, it relates to the improvement of diaryl carbonate yield in the carbonylation reaction.

Diaryl carbonates are valuable intermediates for the preparation of polycarbonates by transesterification with bisphenols in the melt. This method of polycarbonate preparation has environmental advantages over methods which employ phosgene, a toxic gas, as a reagent and environmentally detrimental chlorinated aliphatic hydrocarbons such as methylene chloride as solvents.

Various methods for the preparation of diaryl carbonates by an oxidative carbonylation (hereinafter sometimes simply "carbonylation" for brevity) reaction of hydroxyaromatic compounds with carbon monoxide and oxygen have been disclosed. In general, the carbonylation reaction requires a rather complex catalyst. Reference is made, for example, to U.S. Pat. No. 4,187,242, in which the catalyst is a heavy Group VIII metal; i.e., a Group VIII metal having an atomic number of at least 44, said metals consisting of ruthenium, rhodium, palladium, osmium, iridium and platinum, or a complex thereof. Palladium catalysts have been found particularly useful; they include complexes with phosphines such as triphenylphosphine.

The production of carbonates may frequently be improved by including a metal-based cocatalyst along with the heavy Group VIII metal catalyst. Suitable metal-based cocatalysts have been described broadly in U.S. Pat. Nos. 4,187,242, 4,201,721 and 5,380,907 as compounds or complexes of copper, iron, manganese, cobalt, mercury, lead, cerium, vanadium, uranium, bismuth and chromium. Cerium compounds as cocatalysts are particularly detailed in European patent application 736,512.

Also required in general as part of the catalyst package are halides, typically quaternary ammonium or phosphonium halides, hexaalkylguanidinium halides or alkali metal or alkaline earth metal halides. According to Japanese Kokai 1/165,551 and 8/134,022, the halide can be an iodide; however, product recovery, particularly as defined in terms of "turnover number" (the number of moles of product and specifically diaryl carbonate formed per gram-atom of palladium present) was calculated to be very low, the highest being represented by a turnover number of about 3.3. In the aforementioned European application 736,512, the halide is a chloride or bromide.

Another disadvantage often encountered in the production of diaryl carbonates is the co-production of isomeric compounds. Thus, diphenyl carbonate yields are often decreased by concurrent formation of isomers such as phenyl salicylate and 4-hydroxyphenyl benzoate.

It remains of interest, therefore, to develop catalyst systems which provide improved production of diaryl carbonates. In particular, it is of interest to increase the rate of production relative to amount of catalyst employed and to decrease the proportions of isomers obtained.

SUMMARY OF THE INVENTION

The present invention is based on the discovery that diaryl carbonate production is improved by employing a catalyst material in which Group VIII metals, especially palladium, are used In combination with a bisphosphine and iodide ion.

In one of its aspects, therefore, the invention is a method for preparing a diaryl carbonate which comprises contacting at least one hydroxyaromatic compound with oxygen and carbon monoxide in the presence of an amount effective for carbonylation of at least one catalytic material comprising the following and any reaction products thereof:

(A) a Group VIII metal having an atomic number of at least 44 or a compound thereof, (B) at least one iodide salt, and (C) at least one organic bisphosphine.

Another aspect of the invention is catalyst compositions comprising components A, B and C as described above, and any reaction products thereof.

BRIEF DESCRIPTION OF THE DRAWINGS

The drawings (FIGS. 1–2) are graphical representations of diphenyl carbonate production by the procedures described in the working examples herein.

DETAILED DESCRIPTION; PREFERRED EMBODIMENTS

Figure 1:
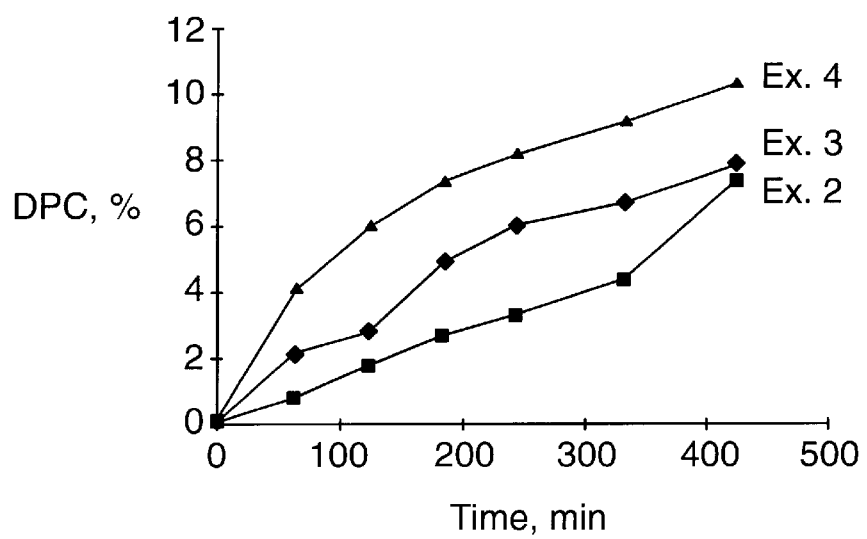

Any hydroxyaromatic compound may be employed in the method of the present invention. Monohydroxyaromatic compounds, such as phenol, the cresols, the xylenols and p-cumylphenol, are generally preferred with phenol being most preferred. The invention may, however, also be employed with dihydroxyaromatic compounds such as resorcinol, hydroquinone and 2,2-bis(4-hydroxyphenyl) propane or "bisphenol A", whereupon the products are polycarbonate oligomers.

Other essential reagents in the diaryl carbonate preparation method of the invention are oxygen and carbon monoxide, which react with the phenol to form the desired diaryl carbonate. They may be employed in high purity form or diluted with another gas such as nitrogen, argon, carbon dioxide or hydrogen which has no negative effect on the reaction.

For the sake of brevity, the constituents of the catalyst system of the invention are defined as "components" irrespective of whether a reaction between said constituents occurs before or during the carbonylation reaction. Thus, the catalyst system may include said components and any reaction products thereof.

Component A of the catalyst system is one of the heavy Group VIII metals, preferably palladium, or a compound thereof. Thus, useful palladium materials include elemental palladium-containing entities such as palladium black, palladium/carbon, palladium/alumina and palladium/silica; palladium compounds such as palladium chloride, palladium bromide, palladium iodide, palladium sulfate, palladium nitrate, palladium acetate and palladium 2,4-pentanedionate; and palladium-containing complexes involving such compounds as carbon monoxide, amines, nitrites, phosphines and olefins. Preferred in many instances are palladium(II) salts of organic acids, most often $C_{2-6}$ aliphatic carboxylic acids, and palladium(II) salts of β-diketones. Palladium(II) acetate and palladium(II) 2,4-pentanedionate are generally most preferred. Mixtures of the aforementioned palladium materials are also contemplated.

Component B is at least one iodide salt. It may be an alkali metal or alkaline earth metal iodide such as lithium iodide, sodium iodide, potassium iodide, calcium iodide or magnesium iodide. Onium, especially tetraalkylammonium, iodides and other iodide salts may also be used, but the alkali metal iodides and especially sodium iodide are preferred.

Component C is at least one organic bisphosphine. By "organic" is meant a compound containing at least one organic radical, with the proviso that said compound may also contain non-organic atoms or radicals. Thus, the bisphosphine may often be characterized by the formula $$(R^1)_2P-R^2-P(R^1)_2, \quad (I)$$

wherein $R^1$ is a monovalent organic radical and $R^2$ is a divalent organic radical. Most often, $R^1$ is an aromatic or alicyclic radical, preferably aromatic and most preferably phenyl.

The identity of the divalent $R^2$ radical is subject to wide variation. It may be aliphatic, as exemplified by ethylene, trimethylene, tetramethylene and neopentylene. It may also be aromatic, as illustrated by phenylene and naphthylene. Suitable radicals include those containing inorganic elements, as illustrated by aminobis(alkylene) and ferrocenylene. For the most part, aliphatic radicals are preferred and $C_{3-8}$ aliphatic radicals especially preferred.

Many bisphosphines of formula I, particularly the ones in which $R^2$ is aliphatic, are commercially available; examples are 1,3-bis(diphenylphosphino)propane and 1,4-bis(diphenylphosphino)butane. Other bisphosphines can be prepared by art-recognized methods.

It is within the scope of the invention to introduce component C, the bisphosphine, into the catalyst mixture as a discrete compound. It is also contemplated to preform a complex of the bisphosphine with the Group VIII metal of component A, whereupon components A and C are introduced as a single entity. This may be achieved, for example, by a ligand interchange reaction between the bisphosphine and a palladium(II) halide complex with another ligand such as acetonitrile.

The preparation of a palladium(II) bisphosphine complex is illustrated by the following example.

EXAMPLE 1

A 100-ml round-bottomed flask was charged with 484.0 mg (1.87 mmol) of commercial grade palladium(II) chloride-acetonitrile complex and 30 ml of acetonitrile. The resulting solution was heated to about 40° C. with vigorous stirring until the palladium salt completely dissolved; a bright orange homogeneous solution resulted. To the stirred solution was added, in one portion, 797.0 mg (1.87 mmol) of 1,4-bis(diphenylphosphino)butane. The phosphine readily dissolved, and a pale yellow precipitate formed instantly. The suspension thus formed was stirred for an additional 5 minutes at room temperature and then cooled in an ice bath for 30 minutes to complete precipitation. The pale yellow precipitate was filtered in air on a medium pore fritted glass filter and washed with reagent grade hexane. It was then dried under vacuum. The yield of the desired palladium(II) chloride bisphosphine complex, whose structure was confirmed by phosphorus-31 nuclear magnetic resonance spectroscopy, was 1.062 g, or 94% of theoretical.

It is also often preferred for the catalyst mixture to contain (D) at least one cerium or lead compound. Cerium is most preferred. Any cerium salt which is found to be active in the catalyst material may be employed. The preferred cerium salts are, for the most part, those of β-diketones and especially 2,4-pentanedionates.

Examples of lead compounds which may be employed are lead oxides such as PbO and $Pb_3O_4$; inorganic lead salts such as lead(II) nitrate; lead carboxylates such as lead(II) acetate and lead(II)propionate; lead alkoxides and aryloxides such as lead(II) methoxide and lead(II) phenoxide; and lead salts of β-diketones such as lead(II) 2,4-pentanedionate. Mixtures of the aforementioned lead compounds may also be employed. The preferred lead compounds are lead(II) oxide, lead(II) aryloxides and lead(II) 2,4-pentanedionate.

In addition to the aforementioned reactants and catalyst system, it is strongly preferred for a desiccant to be present in the reaction system. The preferred desiccants are non-reactive materials such as molecular sieves, as illustrated by 3-Ångstrom (hereinafter "3A") molecular sieves. They are usually isolated from the other reactants, as by presence in a basket mounted to a stirrer shaft or the like.

Component A is most often present in the amount of about 0.1–10,000 ppm by weight of the appropriate Group VIII metal (usually palladium), based on hydroxyaromatic compound. The proportion of component B is generally at least about 20 and preferably at least about 40 equivalents of iodide per gram-atom of metal in component A. It can be up to about 2,000 equivalents on that basis, but there is seldom any advantage in employing more than about 100 equivalents.

Component C is present in an amount effective to form a complex with the metal of component A; this amount is generally at least a number of moles equal to the number of gram-atoms of metal in said component A, and preferably in a ratio of moles of component C to gram-atoms of said metal in the range of about 1.0–1.2:1. Component D, when present, is employed in the amount of about 1–200 gram-atoms of total cerium or lead per gram-atom of the Group VIII metal of component A.

The method of the invention is preferably conducted in a reactor in which the hydroxyaromatic compound and catalyst system are charged under pressure of carbon monoxide and oxygen and heated. The reaction pressure is most often within the range of about 1–500 and preferably about 1–150 atm. Gas is usually supplied in proportions of about 1–50 mole percent oxygen with the balance being carbon monoxide, and in any event outside the explosion range for safety reasons. The gases may be introduced separately or as a mixture. Reaction temperatures in the range of about 60–150° C. are typical. In order for the reaction to be as rapid as possible, it is within the scope of the invention to maintain a substantially constant gas pressure and partial pressure of carbon monoxide and oxygen, as described, for example, in U.S. Pat. No. 5,399,734, until conversion of the hydroxyaromatic compound is complete.

The diaryl carbonates produced by the method of the invention may be isolated by conventional techniques. It is often preferred to form and thermally crack an adduct of the diaryl carbonate with the hydroxyaromatic compound, as described in U.S. Pat. Nos. 5,239,106 and 5,312,955.

According to the present invention, diaryl carbonates can be produced in a very efficient manner as compared with the prior art, especially the aforementioned Japanese Kokai 1/165,551. In particular, high turnover numbers and especially diphenyl carbonate turnover numbers are afforded. It is also found that regioselectivities to diphenyl carbonate are high, the term "regioselectivity" meaning the weight ratio of diphenyl carbonate to total product (i.e., diphenyl carbonate and its isomers) expressed as a percent.

The method of the invention is illustrated by the following examples. All parts are by weight unless otherwise indicated. Minor variations in reagent amounts from one example to another are not believed significant from the standpoint of yield.

EXAMPLES 2–6

A 450-ml Parr reactor of HASTELLOY-C alloy, fitted with a stirrer, was charged at room temperature with 69.8 g (743 mmol) of phenol, various proportions of sodium iodide, 23 ppm by weight (based on phenol) of palladium in a form specified hereinafter, and, in Examples 3–6, cerium(III) 2,4-pentanedionate monohydrate or lead(II) oxide. Molecular sieves (3A, 35 g) were placed in a perforated polytetrafluoroethylene basket mounted to the stir shaft of the reactor.

In Examples 2–4 and 6, the palladium compound employed was a complex (Complex) prepared by the reaction of 1 mole of palladium(II) 2,4-pentanedionate with 1 mole of 1,4-bis(diphenylphosphino)butane. In Example 5, it was the product of Example 1.

The reactor vessel was sealed, purged, and pressurized to 88.4 atm with a mixture of 9% (by volume) oxygen and 91% carbon monoxide. The reactor was then heated to 100° C. over 10 minutes with stirring (1500 rpm). Liquid sampling of the reactor contents was performed periodically at reaction temperature and pressure via a sample dip tube in the reactor. Product aliquots were periodically analyzed by HPLC for diphenyl carbonate (DPC) and its isomers phenyl salicylate (PS) and p-hydroxyphenyl benzoate (HPB), the major proportion of the product mixture being phenol in each instance.

The results are given in the following table, with "TON" designating turnover numbers. Proportions of sodium iodide are in equivalents of iodide per gram-atom of palladium; proportions of cerium salt and lead salt in gram-atoms of metal per gram-atom of palladium. Comparison was made with a control in which the catalyst system contained only palladium(II) 2,4-pentanedionate (Pdacac) and sodium iodide.

What is claimed is:

1. A method for preparing a diaryl carbonate which comprises contacting at least one hydroxyaromatic compound with oxygen and carbon monoxide in the presence of an amount effective for carbonylation of at least one catalytic material comprising the following and any reaction products thereof:
    (A) a Group VIII metal having an atomic number of at least 44 or a compound thereof,
    (B) at least one iodide salt, and
    (C) at least one organic bisphosphine.
2. A method according to claim 1 wherein the iodide salt is present in the amount of at least about 20 equivalents of iodide per gram-atom of metal in component A.
3. A method according to claim 2 wherein the hydroxyaromatic compound is phenol.
4. A method according to claim 3 wherein component C is 1,3-bis(diphenylphosphino)propane.
5. A method according to claim 3 wherein component C is 1,4-bis(diphenylphosphino)butane.
6. A method according to claim 3 wherein the Group VIIIB metal in component A is palladium.
7. A method according to claim 3 wherein component C is introduced into the catalyst composition as a discrete compound.
8. A method according to claim 5 wherein component A is palladium(II) acetate or palladium(II) 2,4-pentanedionate.
9. A method according to claim 3 wherein component C is introduced into the catalyst composition as a complex with the palladium of component A.
10. A method according to claim 2 wherein there is also present (D) at least one cerium or lead compound.

| Example | 2 | 3 | 4 | 5 | 6 | 7 | Control |
|---|---|---|---|---|---|---|---|
| Pd-compound | Complex | Complex | Complex | Ex. 1 | Complex | Complex | Pdacac |
| NaI, amount | 50 | 50 | 100 | 200 | 30 | 50 | 50 |
| Component D (amount) | — | Ce (4) | Ce (8) | Ce (8) | — | Pb (4) | — |
| Time, min | 420 | 420 | 420 | 360 | 300 | 240 | 420 |
| Product: | | | | | | | |
| DPC, % | 7.3 | 7.8 | 10.3 | 6.7 | 4.3 | 4.8 | 4.7 |
| HPB, % | 0.29 | 0.2 | 0.2 | 0.4 | 0.1 | 0.1 | 0.5 |
| PS, % | 0.87 | 0.6 | 0.96 | 1.2 | 0.45 | 0.1 | 1.3 |
| Total TON | 1,953 | 1,816 | 2,526 | 1,808 | 922 | 1,195 | 1,493 |
| DPC TON | 1,685 | 1,647 | 2,262 | 1,457 | 817 | 1,145 | 1,080 |
| Regioselectivity to DPC, % | 86.3 | 90.7 | 89.9 | 80.6 | 88.7 | 95.8 | 72.3 |

A comparison of Examples 2–7 with the control demonstrates the advantages of the invention with regard to diphenyl carbonate production, as measured by percentage in the product mixture, by DPC turnover number and by regioselectivity. Examples 3–5 show an advantage in increasing the proportion of sodium iodide to 100 but a disadvantage in higher values. Example 6 in comparison with the control shows the advantage in effect on turnover number of a sodium iodide proportion of at least 40.

Figure 2:
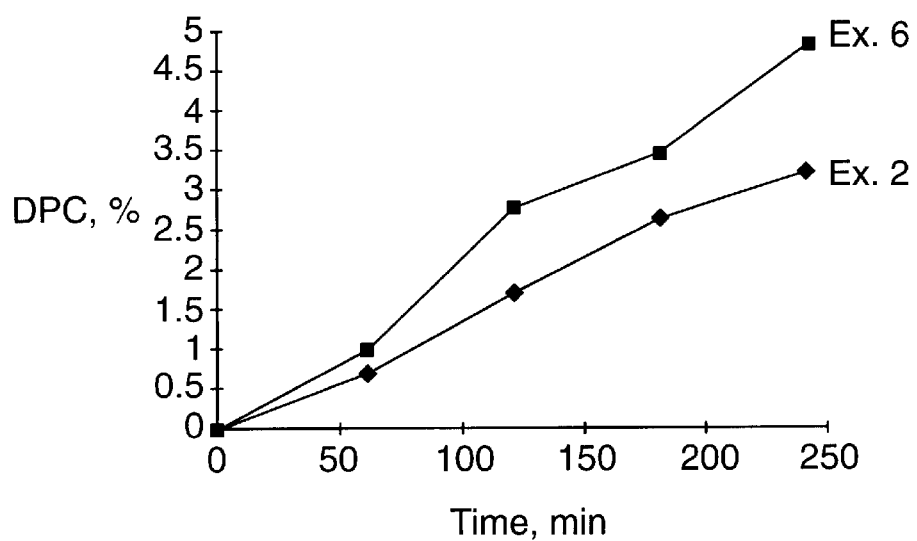

The progress of the reactions of Examples 2–4 and 6 is also demonstrated graphically in FIGS. 1 and 2. FIG. 1 shows the increase in diphenyl carbonate proportion over periods up to 400 minutes as a result of the presence of cerium in the catalyst composition (Examples 2 and 3) and an increase in sodium iodide proportion (Examples 3 and 4). FIG. 2 shows a similar increase over periods up to 240 minutes as a result of the presence of lead in the catalyst composition (Examples 2 and 6).

11. A method according to claim 10 wherein component D is cerium(III) 2,4-pentanedionate or lead(II) oxide.
12. A method according to claim 3 wherein component B is an alkali metal iodide.
13. A method according to claim 12 wherein component B is sodium iodide.
14. A method according to claim 2 wherein a desiccant is also present.
15. A method according to claim 3 wherein component A is present in the amount of about 0.1–10,000 ppm by weight of said Group VIII metal, component B in the amount of about 40–100 equivalents of iodide per gram-atom of metal in component A, component C in a ratio of moles to gram-atoms of said metal in the range of about 1.0–1.2:1.
16. A method according to claim 15 wherein component D is present in the amount of about 1–200 gram-atoms of total cerium or lead per equivalent of the Group VIII metal of component A.

17. A method according to claim 3 wherein the proportion of oxygen is about 1–50 mole percent based on total oxygen and carbon monoxide.

18. A method according to claim 3 wherein a pressure in the range of about 1–500 atm and a temperature in the range of about 60–150° C. are maintained.

19. A method for preparing diphenyl carbonate which comprises contacting phenol with oxygen and carbon monoxide in the presence of an amount effective for carbonylation of at least one catalytic material comprising the following and any reaction products thereof:

(A) palladium or a compound thereof, (B) at least one alkali metal iodide in the amount of about 40–100 equivalents of iodide per gram-atom of palladium in component A, (C) 1,3-bis(diphenylphosphino)propane or 1,4-bis(diphenylphosphino)butane, and (D) at least one cerium or lead compound.

* * * * *